(12) United States Patent
Li et al.

(10) Patent No.: US 9,790,743 B2
(45) Date of Patent: Oct. 17, 2017

(54) NATURAL GAS HYDRATE FORMATION DRILLING SIMULATION DEVICE

(71) Applicant: GUANGZHOU INSTITUTE OF ENERGY CONVERSION, CHINESE ACADEMY OF SCIENCES, Guangzhou, Guangdong Province (CN)

(72) Inventors: Xiaosen Li, Guangzhou (CN); Yu Zhang, Guangzhou (CN); Yi Wang, Guangzhou (CN); Gang Li, Guangzhou (CN); Zhaoyang Chen, Guangzhou (CN); Ningsheng Huang, Guangzhou (CN)

(73) Assignee: GUANGZHOU INSTITUTE OF ENERGY CONVERSION, CHINESE ACADEMY OF SCIENCES, Guangzhou (CN)

( * ) Notice: Subject to any disclaimer, the term of this patent is extended or adjusted under 35 U.S.C. 154(b) by 300 days.

(21) Appl. No.: 14/765,684

(22) PCT Filed: Dec. 8, 2014

(86) PCT No.: PCT/CN2014/093238
§ 371 (c)(1),
(2) Date: Aug. 4, 2015

(87) PCT Pub. No.: WO2016/078165
PCT Pub. Date: May 26, 2016

(65) Prior Publication Data
US 2016/0305205 A1    Oct. 20, 2016

(30) Foreign Application Priority Data

Nov. 20, 2014    (CN) .......................... 2014 1 0675849

(51) Int. Cl.
*E21B 10/00*    (2006.01)
*E21B 41/00*    (2006.01)
(Continued)

(52) U.S. Cl.
CPC .............. *E21B 10/00* (2013.01); *E21B 21/00* (2013.01); *E21B 34/00* (2013.01); *E21B 41/00* (2013.01);
(Continued)

(58) Field of Classification Search
CPC ..... E21B 1/00; E21B 3/00; E21B 7/00; E21B 12/00; E21B 15/00; E21B 17/00; E21B 47/00; E21B 49/00; E21B 2021/007
(Continued)

(56) References Cited

U.S. PATENT DOCUMENTS 4,510,801 A * 4/1985 Quigley .................. E21B 21/06
374/45
6,269,684 B1 * 8/2001 Maki, Jr. ............... E21B 49/005
73/53.01
(Continued)

*Primary Examiner* — Waseem Moorad
*Assistant Examiner* — Lamia Quaim
(74) *Attorney, Agent, or Firm* — Westerman, Hattori, Daniels & Adrian, LLP

(57) ABSTRACT

A natural gas hydrate drilling simulation device, includes a hydrate rock core simulation system, a drilling system, a drilling fluid injection system and a drilling fluid treatment system. The hydrate rock core simulation system includes a hydrate formation simulation wellbore, an artificial rock core, a water bath jacket and low temperature water bath. The drilling system includes a bracket, a high pressure rotary connecting device, a hydraulic device and a drilling device. The drilling fluid injection system includes a mud tank, a drilling fluid flowmeter, mud pumps and an overflow valve. The drilling fluid treatment system includes a high pressure sand remover, a back pressure and overflow control system, a gas-liquid separator, a dyer, a gas flowmeter, a liquid
(Continued)

flowmeter and a mud treatment tank. This natural gas hydrate drilling simulation device performs simulation experiments under a variety of downhole working condition environments.

10 Claims, 2 Drawing Sheets

(51) Int. Cl.
*E21B 21/00* (2006.01)
*E21B 34/00* (2006.01)
*E21B 47/06* (2012.01)
*E21B 47/00* (2012.01)
*E21B 49/00* (2006.01)
*E21B 47/10* (2012.01)
*E21B 43/01* (2006.01)

(52) U.S. Cl.
CPC .......... *E21B 47/00* (2013.01); *E21B 47/0001* (2013.01); *E21B 47/0006* (2013.01); *E21B 47/06* (2013.01); *E21B 47/065* (2013.01); *E21B 47/10* (2013.01); *E21B 49/00* (2013.01); *E21B 2034/002* (2013.01); *E21B 2043/0115* (2013.01)

(58) Field of Classification Search
USPC .................. 175/244, 239, 332, 403, 424
See application file for complete search history.

(56) References Cited

U.S. PATENT DOCUMENTS

2004/0198611 A1* 10/2004 Atkinson ............... C09K 8/665
507/100
2004/0265176 A1* 12/2004 Kerherve ........... B01D 19/0005
422/68.1

* cited by examiner

NATURAL GAS HYDRATE FORMATION DRILLING SIMULATION DEVICE

FIELD OF THE INVENTION

The present invention relates to a drilling simulation device, and more particularly to an experimental simulation device for simulating a natural gas hydrate formation drilling process under different working conditions.

BACKGROUND OF THE INVENTION

A natural gas hydrate (NGH) has the advantages of large reserves, wide distribution, high energy density, cleanness, environmental friendliness and the like, and is considered as the most important clean and alternative energy in the 21st century, thus an NGH research has important scientific and practical significance.

The NGH research includes such aspects as resource investigation and evaluation, exploitation technology, safety and environmental impact and the like. On the basis of resource investigation and research, economic, efficient and safe NGH exploitation technology is a decisive factor in NGH resource development. Contents involved in the research on the NGH exploitation technology mainly include drilling, decomposition, gas production, environmental impact and the like. The NGH drilling technology is the basis and premise of achieving NGH exploitation. At present, reports on simulation research of NGH drilling are few. Although certain permafrost region and marine NGH field exploration sampling drilling and a small amount of test exploration drilling work have been carried out, NGH exploration sampling drilling and production exploration drilling are greatly different, therefore, a research on the NGH exploration drilling technology is crucial to the development and utilization of the NGH resource.

Since the natural gas hydrate is a matter strongly constrained by the environment, the formation and stability thereof require very special high pressure and low temperature environments, in an NGH drilling process, a large amount of heat is generated in a rock cutting process of a drill bit and by the friction of a bottom hole drilling tool with a well wall and a rock core, and formation stress near the well wall and the bottom hole is released, which will decompose NGH to produce a gas and decomposed water. The NGH decomposition causes serve damages to the drilling quality, the drilling speed, the equipment and the like. On one hand, after entering drilling fluid, the gas circulates with the drilling fluid to reduce the density of the drilling fluid, resulting in reduced hydrostatic pressure of the bottom hole and acceleration of the NGH decomposition, and a vicious circle is formed to eventually lead to the decomposition of a large quantity of hydrates in the bottom hole, resulting in such accidents as severe borehole diameter expansion, blowout, borehole collapse, casing deformation, ground settlement and on the like. On the other hand, when drilling in deep sea and frozen earth areas with very low temperatures, temperature and pressure conditions for re-forming the NGH by gas exist at a certain position in a well bore or in a ground pipeline, in this case, the NGH is likely to form in the drilling fluid to block the drilling fluid circulation (similar to natural gas hydrate blockage in an oil and gas transmission pipeline) or other pipelines of a drilling system, resulting in a series of serious accidents in the well. Therefore, it is a key issue related to the development and utilization of the NGH resource that whether bottom hole heat (temperature), pressure and NGH decomposition in the drilling process can be controlled. In addition, since submarine NGH exists in shallow sediments, a hydrate reservoir is weak in geological mechanical property and is low in rupture pressure, so that if the drilling pressure is too high, formation breakdown is generated to result in leakage of the drilling fluid. Therefore, compared with conventional oil and gas exploration drilling, the NGH drilling is very different on such aspects as drilling speed, drilling fluid ratio, pressure change, circulation velocity, bottom hole pressure control method, etc. Before mature and systematic NGH formation drilling theory and related technology are researched and established, if the conventional oil and gas exploration drilling technology is rashly adopted for drilling, unpredictable and uncontrollable safety accidents may be induced.

NGH exploration drilling methods can be divided into three categories: laboratory simulation, numerical simulation and field test, wherein the field test is costly and is only suitable for countries having found NGH physical samples; although the numerical simulation is low in cost, but must be based on basic data and basic laws obtained by the laboratory simulation; while the experimental simulation is to establish experimental simulation instruments and equipment in a laboratory and controls such conditions of the equipment as temperature, pressure, medium and the like to approximately simulate a natural NGH reservoir environment and research the generation, the drilling process rules and the influence mechanism. Since the experimental simulation is low in research cost and is the foundation of other researches, the NGH drilling experimental simulation research becomes the most feasible research method in the current NGH drilling technology research.

At present, the bottleneck problem restricting the development of the NGH drilling experimental simulation research is lack of a detection method and an experimental apparatus for quickly and accurately measuring the phase change and existing characteristics of the NGH in the drilling process in real time and in situ under high pressure and low temperature, this is mainly because the NGH formation conditions (high pressure and low temperature) are harsh and the experimental media are complicated, such that the existing oil and gas drilling simulation device and detection instrument cannot be applied to the NGH drilling simulation research and must be designed and manufactured again to ensure high pressure resistance and high test precision.

SUMMARY OF THE INVENTION

In view of this, aiming at the problems in the natural gas hydrate drilling simulation process in the prior art, it is necessary to provide a device for simulating a simulation research on natural gas hydrate drilling, which can be used for simulating the natural gas hydrate drilling process under low temperature and high pressure and measuring drilling experiments and drilling parameters under different formation conditions and working conditions, so as to optimize a drill bit, a drilling pressure, a rotating speed and a drilling fluid category and evaluate and control risks of the drilling process.

A natural gas hydrate drilling simulation device includes a hydrate rock core simulation system, a drilling system, a drilling fluid injection system and a drilling fluid treatment system, wherein:
the hydrate rock core simulation system comprising a hydrate formation simulation wellbore, an artificial rock core, a water bath jacket and low temperature water bath; wherein the artificial rock core is filled in the inner cavity of the hydrate formation simulation wellbore, the water bath jacket is wrapped on the outer side of the hydrate formation simulation wellbore, and the low temperature water bath is connected with the water bath jacket for controlling the temperature of the internal environment of the hydrate formation simulation wellbore;

the drilling system includes a bracket, a high pressure rotary connecting device, a hydraulic device and a drilling device, wherein the high pressure rotary connecting device is of a hollow structure which is fixedly installed at the upper side of the hydrate formation simulation wellbore, and the hollow structure is communicated with the inner cavity of the hydrate formation simulation wellbore; the bracket includes a base, an upright post, a wellbore fixing bracket, a rotary connector fixing bracket and a motor platform, the upright post is installed at one side of the base, one of the sides of the wellbore fixing bracket, the rotary connector fixing bracket and the motor platform is fixedly connected to the upright post, and the other sides thereof are fixedly connected with the hydrate formation simulation wellbore, the high pressure rotary connecting device and the drilling device, respectively, the drilling device includes a drill pipe, and the drill pipe stretches into the hollow structure of the high pressure rotary connecting device and extends to the inner cavity of the hydrate formation simulation wellbore; the hydraulic device is connected with the drill pipe for providing a necessary downward pressure for the drill pipe; the drilling fluid injection system includes a mud tank, a mud cooling device, a stirring device, a first mud pump, a heater, a second mud pump, a drilling fluid flowmeter and an overflow valve. The inlet pipelines of the first mud pump and the second mud pump are connected with the mud tank, the outlet pipeline of the first mud pump is connected with the heater, the outlet pipeline of the second mud pump is jointed with the outlet pipeline of the heater through a tee joint, and a temperature sensor is arranged at the outlet of the tee joint for measuring the mud temperature. The mixed mud is divided by the tee joint into two paths after being connected, one path is connected with a mud inlet by the drilling fluid flowmeter through a pipeline, and the other path is connected with the mud tank through the overflow valve. The mud tank is provided with the mud cooling device and the stirring device. In an experiment, the second mud pump is started at first to provide two parameters of mud input pressure and mud flow; and then the openness of the overflow valve is adjusted to control and simulate a bottom hole pressure value. Drilling fluid is injected into the drill pipe via the mud pumps, flows out from a drill bit through a one-way valve and flows out from a mud outlet via an annular space between the drill pipe and a drill hole. In the experiment process, the mud flow is controlled by the second mud pump and the overflow valve, and the mud temperature is controlled by a low speed flow pump and the heater.

The drilling fluid treatment system includes a high pressure sand remover, a back pressure and overflow control system, a gas-liquid separator, a gas flowmeter and a liquid flowmeter; the inlet of the high pressure sand remover is connected with a mud outlet formed on the high pressure rotary connecting device, the outlet of the high pressure sand remover is connected with the gas-liquid separator through the back pressure and overflow control system, a gas flowing out from the gas-liquid separator is metered by the gas flowmeter, and liquid flowing out from the gas-liquid separator returns to the mud tank.

The inner cavity of the hydrate formation simulation wellbore is a 1.80 mm×1.80 mm×180 mm cube, and the pressure resistance range is 0-30 MPa.

The hydrate formation simulation wellbore includes a cylinder body, an upper flange and a lower flange, the upper flange and the lower flange are respectively fixed on the upper and lower sides of the cylinder body; the high pressure rotary connecting device is fixed to the upper flange, and a gas-liquid inlet and a gas-liquid outlet communicated with the inner cavity of the hydrate formation simulation wellbore are respectively formed on the upper flange and the lower flange. The gas-liquid inlet can be externally connected with gas injection and liquid injection equipment and a vacuumizing device. The lower flange is provided with a temperature and pressure measurement interface and a stress measurement interface at the same time.

The hydraulic device is composed of an oil tank, a hydraulic oil cylinder and a hydraulic pump, one end of the hydraulic pump is connected with the oil tank through an oil pipe, the other end of the hydraulic pump is connected with the hydraulic oil cylinder, and the hydraulic oil cylinder provides a necessary drilling downward pressure.

The drilling device further includes a servo motor, a first gear, a second gear and a drill bit, the servo motor is installed on the motor platform, the rotating shaft of the servo motor is connected with the first gear, and the second gear engaged with the first gear is fixedly sleeved on the drill pipe; the output end of the drill pipe is connected with the drill bit, the drill pipe is of a hollow cavity structure, a one-way valve is installed in the hollow cavity, the outside diameter of the drill pipe is smaller than the inside diameter of the hollow structure of the high pressure rotary connecting device, and a hole formed on the surface of the drill pipe is used for injecting the drilling fluid into the hollow cavity of the drill pipe through the mud inlet.

The maximum drilling distance of the drill bit in the artificial rock core is 150 mm, the diameter of the drill bit is 25 mm, and the diameter of the drill pipe is 16 mm.

The high pressure rotary connecting device is composed of a gland, an upper guide sleeve, a first composite movable sealing ring, a rotary connector cylinder body, a lower guide sleeve, a second composite movable sealing ring, a lower pressing sleeve, a snap ring, a high pressure ball valve, a mud inlet and a mud outlet, the upper guide sleeve is fixed at the upper end of the high pressure rotary connecting device, the first composite movable sealing ring and the second composite movable sealing ring are arranged at a gap between the hollow structure of the high pressure rotary connecting device and the drill pipe, the first composite movable sealing ring is located at the upper side of the mud inlet and is fixed to the upper guide sleeve, the second composite movable sealing ring is located between the mud inlet and the mud outlet, the upper end of the lower pressing sleeve is fixed to the second composite movable sealing ring and is used for pressing the second composite movable sealing ring, meanwhile is fixed at the outer side of the upper end of the lower pressing sleeve through the snap ring, and the lower end of the lower pressing sleeve is fixed to the upper flange through a bolt.

The high pressure ball valve is arranged at a position located at the joint with the hydrate formation simulation wellbore on the bottom of the hollow structure of the high pressure rotary connecting device, and the high pressure ball valve is at a closed state before the drilling process is started.

The artificial rock core is prepared by mixing quartz sand with epoxy resin and pressing, the size of the artificial rock core is consistent with the size of the inner cavity of the hydrate formation simulation wellbore, temperature and pressure measurement points are arranged in the artificial rock core, stress measurement points are arranged on the inner wall of one side of the hydrate formation simulation wellbore, and sensors corresponding to the temperature and pressure measurement points and the stress measurement points are led to the outside of the hydrate formation simulation wellbore through the measurement interface on the lower flange via leads.

Three detection layers are arranged in the artificial rock core along the height direction of the hydrate formation simulation wellbore, which are respectively an upper detection layer, a middle detection layer and a lower detection layer corresponding to the interior of the hydrate layer; the three detection layers equally divide the inner cavity of the hydrate formation simulation wellbore into 4 parts; each detection layer plane is divided into 36 mm×36 mm grids, and a temperature measurement sensor and a pressure sensor are arranged at each grid node.

Nine stress measurement points are distributed on the inner wall of one side of the hydrate formation simulation wellbore, and the 9 stress measurement points are uniformly distributed on the inner wall in a 3×3 distribution manner.

The natural gas hydrate drilling simulation device further includes a detection system, the detection system is mainly composed of a drilling parameter detection system and a rock core parameter detection system, wherein the drilling parameter detection system is mainly composed of a drilling pressure sensor, a torque sensor, a rotating speed sensor and a drilling footage sensor, and the rock core parameter detection system is mainly composed of a pressure sensor, a temperature sensor and a stress sensor. The other measurement parameters further include drilling fluid flow, gas flow or the like. The measured data may be collected and recorded by a data collector and a computer.

To sum up, the present invention has the advantages that: the natural gas hydrate drilling simulation device in the present invention can be used for measuring the change and distribution of temperature and pressure of a hydrate simulation layer in the drilling process in real time. The experimental device can be used for detecting the stress change condition of the hydrate layer in the drilling process. After a simulation experiment, the rock core can be taken out to analyze the damage conditions of the well wall and the rock core.

The natural gas hydrate drilling simulation device in the present invention can be used for simulating different hydrate rock core conditions, different drilling speeds and different drilling fluid proportion conditions, controlling the flow rate and the temperature of the drilling fluid in the drilling process to meet the requirements of different working conditions, and comprehensively evaluating the hydrate formation drilling process.

The natural gas hydrate drilling simulation device in the present invention can be used for performing relevant simulation experiments under a variety of downhole working condition environments and has the advantages of convenient operation and simple structure, so as to provide indoor experimental data for evaluation of safety control of natural gas hydrate drilling and formulation of a drilling solution.

Figure 1:
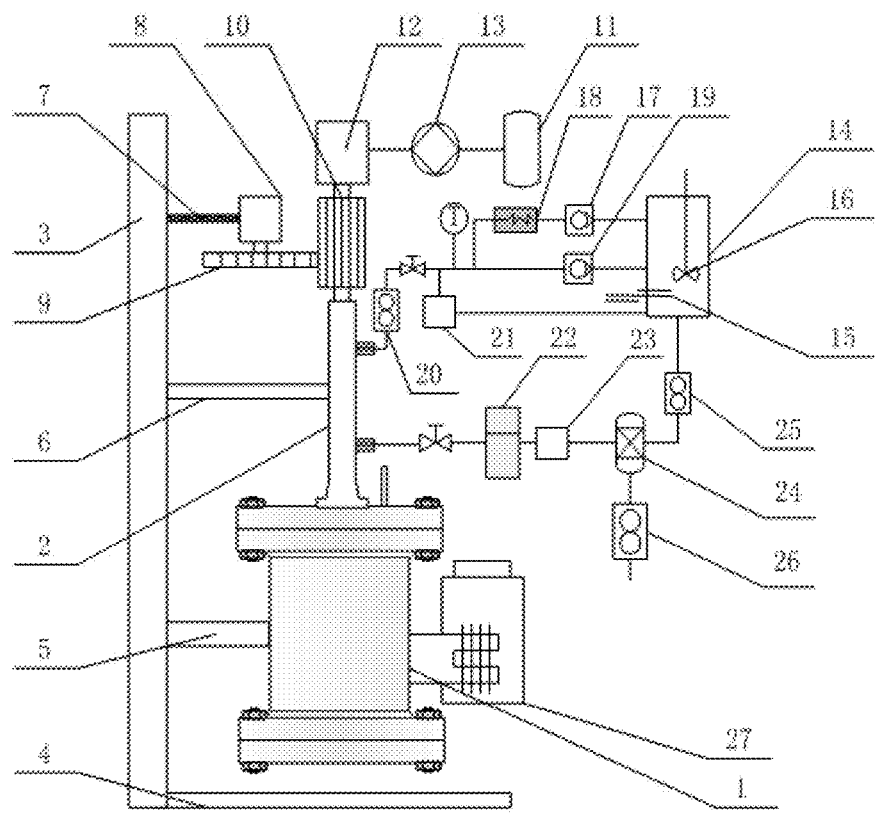
FIG. 1 is a schematic diagram of a structure of an embodiment of a natural gas hydrate drilling simulation device in the present invention.

REFERENCE NUMERALS 1. hydrate formation simulation wellbore; 2. high pressure rotary connecting device; 3. upright post; 4. base; wellbore fixing bracket; 6. rotary connector fixing bracket; 7. motor platform; 8. servo motor; 9. gear; 10. gear; 11. oil tank; 12. hydraulic oil cylinder; 13. hydraulic pump; 14. mud tank; 15. mud cooling device; 16. stirring device; 17. mud pump; 18. heater; 19. mud pump; 20. drilling fluid flowmeter; 21. overflow valve; 22. high pressure sand remover; 23. back pressure and overflow control system; 24. gas-liquid separator; 25. liquid flowmeter; 26. gas flowmeter; 27. low temperature water bath; 28. gas-liquid inlet; 29. temperature and pressure measurement duct; 30. water bath jacket; 31. upper flange; 32. cylinder body; 33. lower flange; 34. gas-liquid outlet; 35. artificial rock core; 36. gland; 37. upper guide sleeve; 38. composite movable sealing ring; 39. rotary connector cylinder body; 40. lower guide sleeve; 41. composite movable sealing ring; 42. lower pressing sleeve; 43. snap ring; 44. mud inlet; 45. mud outlet; 46. drill pipe; 47. drill bit; 48. one-way valve; 49. high pressure ball valve.

DETAILED DESCRIPTION OF THE EMBODIMENTS

To better understand the present invention, a further description of the present invention will be given below in combination with the accompanying drawings, but the embodiment of the present invention is not limited thereto.

Embodiment

A natural gas hydrate drilling simulation device in the present invention can be used for performing simulation experiments on a natural gas hydrate formation drilling process under different rock core properties, hydrate saturability and different drilling conditions, so as to optimize the drilling conditions and comprehensively evaluate risks of drilling process.

Figure 2:
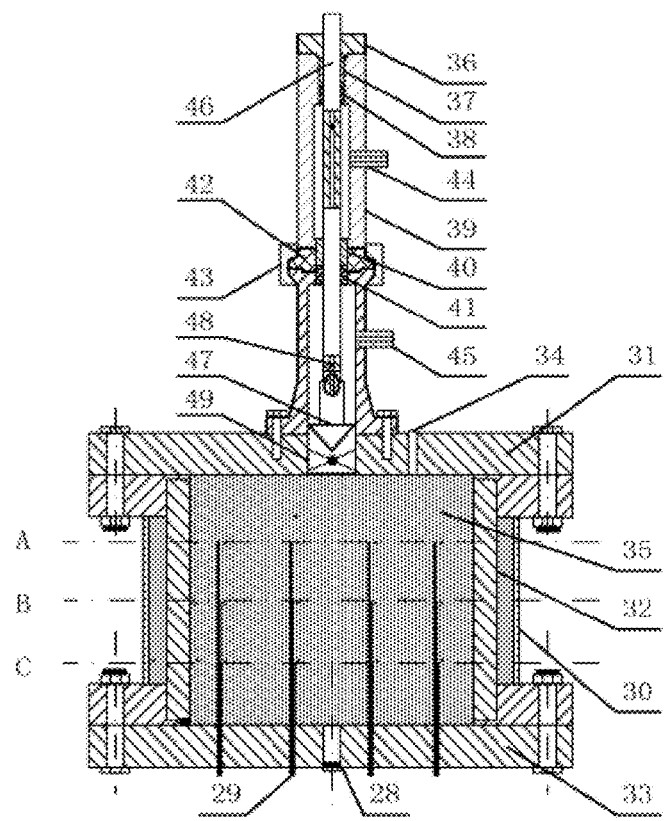
FIG. 2 is a schematic diagram of sectional structures of a hydrate formation simulation wellbore and a high pressure rotary connecting device in the embodiment of the present invention.
Figure 3:
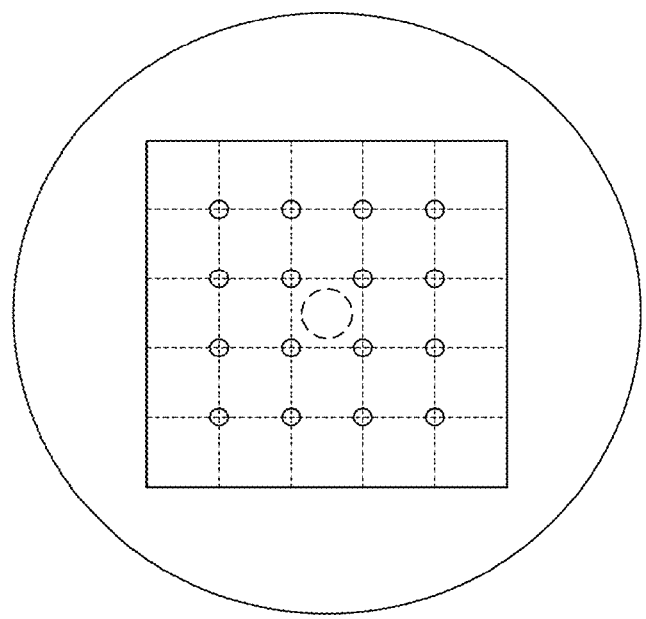
FIG. 3 is a schematic diagram of sectional structures in a B direction in FIG. 2.

Please see FIG. 1 to FIG. 3, the natural gas hydrate drilling simulation device includes a hydrate rock core simulation system, a drilling system, a drilling fluid injection system, a drilling fluid treatment system and a detection system.

The hydrate rock core simulation system includes a hydrate formation simulation wellbore 1, an artificial rock core 35, a water bath jacket 30 and low temperature water bath 27. The interior of the hydrate formation simulation wellbore 1 is a 180 mm×180 mm×180 mm cube, and the pressure resistance range is generally 0-30 MPa. The inner cavity of the hydrate formation simulation wellbore 1 is formed by an upper flange 31, a cylinder body 32 and a lower flange 33, which are fixed and sealed by a plurality of bolts. A gas-liquid inlet 28 is formed in the middle of the lower flange 33, a gas-liquid outlet 34 is formed in the upper flange 31, and the gas-liquid inlet 28 can be connected with gas injection and liquid injection equipment and a vacuumizing device. The lower flange 33 is provided with a temperature and pressure measurement interface and a stress measurement interface at the same time, wherein the temperature and pressure measurement interface is correspondingly provided with a temperature and pressure measurement duct 29 for connecting a temperature or pressure sensor at a temperature and pressure measurement point to the outside of the hydrate formation simulation wellbore 1 through a lead, and similarly, the stress measurement interface is provided with a stress measurement duct.

The artificial rock core 35 is prepared by mixing quartz sand with epoxy resin and pressing, the size of the artificial rock core is consistent with the size of the inner cavity of the hydrate formation simulation wellbore 1, temperature and pressure measurement points are arranged in the artificial rock core 35, stress measurement points are arranged on one side of the inner wall of the hydrate formation simulation wellbore 1, and the temperature and pressure measurement points and the stress measurement points are led to the outside of the hydrate formation simulation wellbore 1 through the measurement interface on the lower flange 33 via leads. After a natural gas and working fluid are injected into the artificial rock core 35, a hydrate layer is formed in the cavity. In order to collect the states at various positions in the hydrate layer in the cavity, the hydrate layer is divided into three detection layers along the depth direction, which are respectively an upper detection layer, a middle detection layer and a lower detection layer corresponding to the interior of the hydrate layer. The three detection layers equally divide the inner cavity of the hydrate formation simulation wellbore into 4 parts; 16 temperature and pressure measurement points are respectively arranged on each detection layer plane; each detection layer plane is divided into 36 mm×36 mm grids, and each measurement point is located at the grid node. Nine stress measurement points are distributed on one side of the inner wall of the hydrate formation simulation wellbore 1 and are uniformly distributed on the inner wall in a 3×3 distribution manner.

The water bath jacket 30 is wrapped on the outer side of the hydrate formation simulation wellbore, and the water bath jacket 30 is connected with the low temperature water bath 27 for controlling the temperature of the internal environment of the hydrate formation simulation wellbore 1. The entire experimental device is placed in a low temperature chamber for increasing the stability of the operating temperature of the system.

The drilling system includes a bracket, a high pressure rotary connecting device 2, a hydraulic device and a drilling device, the bracket includes a base 4, an upright post 3, a wellbore fixing bracket 5, a rotary connector fixing bracket 6 and a motor platform 7, the upright post 3 is installed on both sides of the base 4, and the wellbore fixing bracket 5, the rotary connector fixing bracket 6 and the motor platform 7 are installed on the upright post 3.

The high pressure rotary connecting device 2 is composed of a gland 36, an upper guide sleeve 37, a composite movable sealing ring 38, a rotary connector cylinder body 39, a lower guide sleeve 40, a composite movable sealing ring 41, a lower pressing sleeve 42, a snap ring 43, a high pressure ball valve 49, a mud inlet 44 and a mud outlet 45. The upper guide sleeve 37 is fixed at the upper end of the high pressure rotary connecting device 2, the composite movable sealing ring 38 and the composite movable sealing ring 41 are arranged at a gap between the hollow structure of the high pressure rotary connecting device 2 and a drill pipe 46, the composite movable sealing ring 38 is located at the upper side of the mud inlet 44 and is fixed to the upper guide sleeve 37, the composite movable sealing ring 41 is located between the mud inlet 44 and the mud outlet 45, mud enters the hollow structure of the high pressure rotary connecting device 2 between the composite movable sealing ring 38 and the composite movable sealing ring 41, enters the hollow cavity of the drill pipe 46 through an open pore in the surface of a corresponding position of the drill pipe 46, and then flows to a drill bit 47 through a one-way valve 48, the upper end of the lower pressing sleeve 42 is fixed to the composite movable sealing ring 41 and is used for pressing the composite movable sealing ring 41, meanwhile is fixed at the outer side of the upper end of the lower pressing sleeve 42 through the snap ring 43, and the lower end of the lower pressing sleeve 42 is fixed to the upper flange 31 through a bolt, the high pressure ball valve 49 is arranged at a position located at the joint with the hydrate formation simulation wellbore 1 on the bottom of the hollow structure of the high pressure rotary connecting device 2, and the high pressure ball valve 49 is at a closed state before the drilling process is started. The hydraulic device is composed of an oil tank 11, a hydraulic oil cylinder 12 and a hydraulic pump 13, one end of the hydraulic pump 13 is connected with the oil tank 11 through an oil pipe, the other end of the hydraulic pump is connected with the hydraulic oil cylinder 12, and the hydraulic oil cylinder 12 provides a necessary drilling downward pressure.

The drilling device is composed of a servo motor 8, a gear 9, a gear 10, the drill pipe 46 and the drill bit 47, the drilling device further includes a servo motor 8, a gear 9, a gear 10 and the drill bit 47, the servo motor 8 is installed on the motor platform 7, the rotating shaft of the servo motor 8 is connected with the gear 9, and the gear 10 engaged with the gear 9 is fixedly sleeved on the drill pipe 46; the output end of the drill pipe 46 is connected with the drill bit 47, the drill pipe 46 is of a hollow cavity structure, the one-way valve 48 is installed in the hollow cavity, the outside diameter of the drill pipe 46 is smaller than the inside diameter of the hollow structure of the high pressure rotary connecting device 2, and a hole formed on the surface of the drill pipe 46 is used for injecting the drilling fluid into the hollow cavity of the drill pipe 46 through the mud inlet 44. The maximum drilling distance of the drill bit 47 in the artificial rock core is 150 mm, the diameter of the drill bit is 25 mm, and the diameter of the drill pipe 46 is 16 mm.

The drilling fluid injection system includes a mud tank 14, a mud cooling device 15, a stirring device 16, a low speed mud pump 17, a heater 18, a high speed mud pump 19, a drilling fluid flowmeter 20 and an overflow valve 21. The inlet pipelines of the mud pump 17 and the mud pump 19 are connected with the mud tank 14, and the outlet pipeline of the mud pump 17 is connected with the inlet pipeline of the heater 18. A tee joint includes an inlet and two outlets, wherein the inlet joints the outlet pipeline of the mud pump 19 with the outlet pipeline of the heater 18, namely the mud in the mud tank 14 conveyed by the mud pump 17 and the mud pump 19 is conveyed to the inlet of the tee joint after being mixed, the mixed mud is divided by the tee joint into two paths after being connected, one path is connected with the mud inlet 44 by the drilling fluid flowmeter 20 through a pipeline, and the other path is connected with the mud tank 14 through the overflow valve 21. A temperature sensor is arranged at the outlet (of course can also be the inlet of the tee joint) of the tee joint for measuring the mud temperature. The mud tank 14 is provided with the mud cooling device 15 and the stirring device 16. In an experiment, the mud pump 19 is started at first to provide two parameters of mud input pressure and mud flow; and then the openness of the overflow valve 21 is adjusted to control and simulate a bottom hole pressure value. Drilling fluid is injected into the drill pipe 46 via the mud pump 19, flows out from the drill bit 47 through the one-way valve 48 and flows out from the mud outlet 45 via an annular space between the drill pipe 46 and a drill hole. In the experiment process, the mud flow is controlled by the mud pump 19 and the overflow valve, and the mud temperature is controlled by the mud pump 17 and the heater 18.

The drilling fluid treatment system includes a high pressure sand remover 22, a back pressure and overflow control system 23, a gas-liquid separator 24, a liquid flowmeter 25 and a gas flowmeter 26. The inlet of the high pressure sand remover 22 is connected with the mud outlet 45 formed on the high pressure rotary connecting device 2 through a pipeline, and the outlet of the high pressure sand remover 22 is connected with the back pressure and overflow control system 23 and the gas-liquid separator 24. A gas flowing out from the gas-liquid separator 24 is metered by the gas flowmeter 26, and liquid returns to the mud tank 14 through the liquid flowmeter 25.

The detection system is mainly composed of a drilling parameter detection system and a rock core parameter detection system, wherein the drilling parameter detection system is mainly composed of a drilling pressure sensor, a torque sensor, a rotating speed sensor and a drilling footage sensor, and the rock core parameter detection system is mainly composed of a pressure sensor, a temperature sensor and a stress sensor. The other measurement parameters further include drilling fluid flow, gas flow and the like. The measured data may be collected and recorded by a data collector and a computer.

It should be understood that, the application of the present invention is not limited to the examples mentioned above, those of ordinary skill in the art can make improvements or variations according to the above-mentioned illustration, and all these improvements and variations shall fall within the protection scope of the appended claims of the present invention.

The invention claimed is:

1. A natural gas hydrate drilling simulation device, comprising:
    a hydrate rock core simulation system;
    a drilling system;
    a drilling fluid injection system; and
    a drilling fluid treatment system,
    wherein the hydrate rock core simulation system comprises:
    a hydrate formation simulation wellbore;
    an artificial rock core filling in an inner cavity of the hydrate formation simulation wellbore;
    a water bath jacket wrapped on an outer side of the hydrate formation simulation wellbore; and
    a low temperature water bath connected with the water bath jacket for controlling the temperature of an internal environment of the hydrate formation simulation wellbore,
    wherein the drilling system comprises:
    a bracket having a base, an upright post, a wellbore fixing bracket, a rotary connector fixing bracket and a motor platform, the upright post being installed at one side of the base;
    a high pressure rotary connecting device of a hollow structure which is fixedly installed at an upper side of the hydrate formation simulation wellbore, the hollow structure communicating with the inner cavity of the hydrate formation simulation wellbore;
    a drilling device having a drill pipe stretching into the hollow structure of the high pressure rotary connecting device and extending to the inner cavity of the hydrate formation simulation wellbore; and
    a hydraulic device connected with the drill pipe for providing a downward pressure for the drill pipe,
    wherein one of the sides of the wellbore fixing bracket, the rotary connector fixing bracket and the motor platform is fixedly connected to the upright post, and the other sides of the wellbore fixing bracket, the rotary connector fixing bracket and the motor platform are fixedly connected with the hydrate formation simulation wellbore, the high pressure rotary connecting device and the drilling device respectively,
    wherein the drilling fluid injection system comprises:
    a mud tank;
    a mud cooling device arranged in the mud tank;
    a stirring device arranged in the mud tank;
    a first mud pump;
    a second mud pump, with inlet pipelines of the first mud pump and the second mud pump being connected with the mud tank;
    a heater, with an outlet pipeline of the first mud pump being connected with an inlet pipeline of the heater, an outlet pipeline of the second mud pump being jointed with an outlet pipeline of the heater through a tee joint, a temperature sensor being arranged at an outlet of the tee joint for measuring the mud temperature, and mixed mud being divided by the tee joint into two paths after being connected;
    a drilling fluid flowmeter; and
    an overflow valve, wherein one path of the two paths for the mixed mud divided by the tee joint is connected with a mud inlet by the drilling fluid flowmeter through a pipeline, and the other path of the two paths for the mixed mud divided by the tee joint is connected with the mud tank through the overflow valve,
    wherein the drilling fluid treatment system comprises:
    a high pressure sand remover having an inlet and an outlet, the inlet being connected with a mud outlet formed on the high pressure rotary connecting device through a pipeline;
    a back pressure and overflow control system;
    a gas-liquid separator, with the outlet of the high pressure sand remover being connected with the gas-liquid separator through the back pressure and overflow control system;
    a liquid flowmeter, with liquid flowing out from the gas-liquid separator returning to the mud tank through the liquid flowmeter; and
    a gas flowmeter metering a gas flowing out from the gas-liquid separator.

2. The natural gas hydrate drilling simulation device of claim 1, wherein the inner cavity of the hydrate formation simulation wellbore is a 180 mm×180 mm×180 mm cube, and a pressure resistance range is 0-30 MPa.

3. The natural gas hydrate drilling simulation device of claim 2,
    wherein the hydrate formation simulation wellbore comprises a cylinder body, an upper flange and a lower flange, the upper flange and the lower flange are respectively fixed on upper and lower sides of the cylinder body,
    wherein the high pressure rotary connecting device is fixed to the upper flange, and a gas-liquid inlet and a gas-liquid outlet communicated with the inner cavity of the hydrate formation simulation wellbore are respectively formed on the lower flange and the upper flange.

4. The natural gas hydrate drilling simulation device of claim 3,
  wherein the drilling device further comprises a servo motor, a first gear, a second gear and a drill bit, the servo motor is installed on the motor platform, the rotating shaft of the servo motor is connected with the first gear, and the second gear engaged with the first gear is fixedly sleeved on the drill pipe, and
  wherein an output end of the drill pipe is connected with the drill bit, the drill pipe is of a hollow cavity structure, a one-way valve is installed in the hollow cavity, an outside diameter of the drill pipe is smaller than an inside diameter of the hollow structure of the high pressure rotary connecting device, and a hole formed on a surface of the drill pipe is used for injecting a drilling fluid into the hollow cavity of the drill pipe through the mud inlet.

5. The natural gas hydrate drilling simulation device of claim 4, wherein a maximum drilling distance of the drill bit in the artificial rock core is 150 mm, a diameter of the drill bit is 25 mm, and a diameter of the drill pipe is 16 mm.

6. The natural gas hydrate drilling simulation device of claim 4, wherein the high pressure rotary connecting device includes a gland, an upper guide sleeve, a first composite movable sealing ring, a rotary connector cylinder body, a lower guide sleeve, a second composite movable sealing ring, a lower pressing sleeve, a snap ring, a high pressure ball valve, a mud inlet and a mud outlet, the upper guide sleeve is fixed at the upper end of the high pressure rotary connecting device, the first composite movable sealing ring and the second composite movable sealing ring are arranged at a gap between the hollow structure of the high pressure rotary connecting device and the drill pipe, the first composite movable sealing ring is located at the upper side of the mud inlet and is fixed to the upper guide sleeve, the second composite movable sealing ring is located between the mud inlet and the mud outlet, the upper end of the lower pressing sleeve is fixed to the second composite movable sealing ring and is used for pressing the second composite movable sealing ring, meanwhile is fixed at the outer side of the upper end of the lower pressing sleeve through the snap ring, and the lower end of the lower pressing sleeve is fixed to the upper flange through a bolt.

7. The natural gas hydrate drilling simulation device of claim 6, wherein the high pressure ball valve is arranged at a position located at the joint with the hydrate formation simulation wellbore on the bottom of the hollow structure of the high pressure rotary connecting device, and the high pressure ball valve is at a closed state before a drilling process is started.

8. The natural gas hydrate drilling simulation device of claim 2, wherein the artificial rock core is mixed and pressed quartz sand and epoxy resin, a size of the artificial rock core is consistent with a size of the inner cavity of the hydrate formation simulation wellbore, temperature and pressure measurement points are arranged in the artificial rock core, stress measurement points are arranged on the inner wall of one side of the hydrate formation simulation wellbore, and sensors corresponding to the temperature and pressure measurement points and the stress measurement points are led to an outside of the hydrate formation simulation wellbore through the measurement interface on the lower flange via leads.

9. The natural gas hydrate drilling simulation device of claim 8, wherein three detection layers are arranged in the artificial rock core along a height direction of the hydrate formation simulation wellbore, which are respectively an upper detection layer, a middle detection layer and a lower detection layer corresponding to the interior of the hydrate layer,
  wherein the three detection layers equally divide the inner cavity of the hydrate formation simulation wellbore into 4 parts, and
  wherein a detection layer plane of each of the three detection layers is divided into 36 mm×36 mm grids, and a temperature measurement sensor and a pressure sensor are arranged at each grid node in the grids.

10. The natural gas hydrate drilling simulation device of claim 8, wherein nine stress measurement points are distributed on the inner wall of one side of the hydrate formation simulation wellbore, and the nine stress measurement points are uniformly distributed on the inner wall in a 3×3 distribution manner.

* * * * *